(12) United States Patent
Akca et al.

(10) Patent No.: US 11,205,777 B2
(45) Date of Patent: *Dec. 21, 2021

(54) THIN CATHODE FOR MICRO-BATTERY

(71) Applicants: INTERNATIONAL BUSINESS MACHINES CORPORATION, Armonk, NY (US); ASELSAN Elektronik Sanayi ve Ticaret A.Ş., Yenimahalle/Ankara (TR)

(72) Inventors: Esin Akca, San Jose, CA (US); Cagla Akgun, San Jose, CA (US); Gokhan Demirci, San Jose, CA (US); Damon B. Farmer, White Plains, NY (US); Shu-Jen Han, Cortlandt Manor, NY (US); Hareem T. Maune, San Jose, CA (US); Dahyun Oh, San Jose, CA (US)

(73) Assignees: INTERNATIONAL BUSINESS MACHINES CORPORATION, Armonk, NY (US); ASELSAN ELEKTRONIK SANAY VE TICARET A.S., Yenimahalle/Ankara (TR)

( * ) Notice: Subject to any disclaimer, the term of this patent is extended or adjusted under 35 U.S.C. 154(b) by 217 days.

This patent is subject to a terminal disclaimer.

(21) Appl. No.: 16/685,122

(22) Filed: Nov. 15, 2019

(65) Prior Publication Data
US 2020/0083535 A1 Mar. 12, 2020

Related U.S. Application Data

(63) Continuation of application No. 15/629,893, filed on Jun. 22, 2017, now Pat. No. 10,566,623.

(51) Int. Cl.
*H01M 4/583* (2010.01)
*C07C 43/11* (2006.01)
(Continued)

(52) U.S. Cl.
CPC .......... *H01M 4/583* (2013.01); *C01B 32/186* (2017.08); *C07C 43/11* (2013.01); *C07F 1/02* (2013.01);
(Continued)

(58) Field of Classification Search
None
See application file for complete search history.

(56) References Cited

U.S. PATENT DOCUMENTS

| 5,338,625 | A | 8/1994 | Bates et al. |
| 5,510,209 | A | 4/1996 | Abraham et al. |

(Continued)

FOREIGN PATENT DOCUMENTS

| CN | 101937994 | 1/2011 |
| CN | 104659375 | 5/2015 |

(Continued)

OTHER PUBLICATIONS

List of IBM Patents or Patent Applications Treated as Related dated Nov. 15, 2019, 2 pages.

(Continued)

*Primary Examiner* — Daniel S Gatewood
(74) *Attorney, Agent, or Firm* — Tutunjian & Bitetto, P.C.; Randall Bluestone

(57) ABSTRACT

Batteries include an anode, an electrolyte having a high solubility for lithium ions and oxygen, and a cathode formed on a substrate. Lithium ions migrate from the anode through the electrolyte to form $Li_2O_2$ at a surface of the cathode. A current collector positioned in the electrolyte, the electrolyte separating the anode from the cathode.

20 Claims, 3 Drawing Sheets

(51) Int. Cl.

| | | |
|---|---|---|
| *C08F 220/06* | (2006.01) | |
| *C07F 1/02* | (2006.01) | |
| *H01M 10/0568* | (2010.01) | |
| *H01M 4/38* | (2006.01) | |
| *C01B 32/186* | (2017.01) | |
| *H01M 10/0569* | (2010.01) | |
| *H01M 4/66* | (2006.01) | |
| *C01D 15/10* | (2006.01) | |

(52) U.S. Cl.
CPC ........... *C08F 220/06* (2013.01); *H01M 4/382* (2013.01); *H01M 4/661* (2013.01); *H01M 10/0568* (2013.01); *H01M 10/0569* (2013.01); *C01D 15/10* (2013.01)

(56) References Cited

U.S. PATENT DOCUMENTS

| | | |
|---|---|---|
| 8,652,692 B2 | 2/2014 | Visco et al. |
| 8,691,441 B2 | 4/2014 | Zhamu et al. |
| 8,795,899 B2 | 8/2014 | Liu et al. |
| 2010/0143798 A1 | 6/2010 | Zhamu et al. |
| 2011/0287316 A1 | 11/2011 | Lu et al. |
| 2012/0045688 A1 | 2/2012 | Liu et al. |
| 2013/0052547 A1 | 2/2013 | Ogino et al. |
| 2015/0229012 A1 | 8/2015 | Toyoda et al. |

FOREIGN PATENT DOCUMENTS

| | | |
|---|---|---|
| CN | I06328937 | 1/2017 |
| CN | 106469825 | 3/2017 |
| JP | 2013051169 A | 3/2013 |
| JP | 2013073765 A | 4/2013 |
| JP | 2014022281 A | 2/2014 |
| JP | 2014053270 A | 3/2014 |
| JP | 2014063711 A | 4/2014 |
| WO | 2015153995 | 10/2015 |
| WO | 2016002277 A1 | 1/2016 |
| WO | 2017013379 A1 | 1/2017 |

OTHER PUBLICATIONS

Office Action from related Japanese Application No. 2019-568751 dated Apr. 28, 2021, 8 pages.

Colin M. Burke et al., Enhancing electrochemical intermediate solvation through electrolyte anion selection to increase nonaqueous Li—O2 battery capacity, PNAS, Jul. 2015, pp. 9293-9298, vol. 112.

Gints Kucinskis et al., Graphene in lithium ion battery cathode materials: A review, Journal of Power Sources, Oct. 2013, pp. 66-79.

Yongliang Li et al., Superior energy capacity of graphene nanosheets for a nonaqueous lithium-oxygen battery, CHEm. Commun., Jul. 2011, pp. 9438-9440.

Rinaldo Raccichini et al., The role of graphene for electrochemical energy storage, Nature Materials, Mar. 2015, pp. 271-279.

THIN CATHODE FOR MICRO-BATTERY

BACKGROUND

Technical Field

The present invention generally relates to batteries and, more particularly, to the use of a thin carbon cathode in lithium-oxygen batteries.

Description of the Related Art

Lithium-ion batteries are prevalent in fields such as consumer electronics, automobiles, medical devices, and home energy storage. In a lithium ion insertion reaction, the number of lithium ions that can be inserted into a host cathode determines the amount of energy stored in the battery. As a result, a large cathode is needed to increase the storage capacity of the battery. There is therefore a limit to how small an effective lithium ion battery can be made while providing a useful energy density.

Lithium-oxygen battery chemistries have a higher gravimetric and volumetric energy density (e.g., about 3,213 Wh/kg and about 7,422 Wh/L respectively with respect to only cathode mass or volume) than one of the most commonly used cathode materials, $LiCoO_2$ (e.g., about 1,095 Wh/kg and about 5,543 Wh/L respectively with respect to only cathode mass or volume). Lithium-oxygen batteries therefore present a path toward further miniaturization, decreasing the weight and volume of batteries without sacrificing energy capacity. However, existing lithium-oxygen battery implementations use large, porous cathodes that still impose a volumetric disadvantage for miniaturized applications.

SUMMARY

A battery includes an anode, an electrolyte having a high solubility for lithium ions and oxygen, and a cathode formed on a substrate. Lithium ions migrate from the anode through the electrolyte to form $Li_2O_2$ at a surface of the cathode. A current collector positioned in the electrolyte, the electrolyte separating the anode from the cathode.

A battery includes an anode, an electrolyte having a high solubility for lithium ions and oxygen, a current collector in the electrolyte formed from a metal mesh. The battery also includes a current collector in the electrolyte formed from a metal mesh and a cathode formed on a substrate from a single- or double-layer graphene material. Lithium ions migrate from the lithium anode through the electrolyte to form $Li_2O_2$ at a surface of the thin graphene cathode.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein.

DETAILED DESCRIPTION

Embodiments of the present invention employ a thin cathode layer formed from, e.g., graphene with a thickness of a few atoms to form lithium-oxygen batteries to use as a nucleation seed for a solution-mediated lithium-oxygen battery discharge reaction. The present embodiments thereby provide a cathode capacity of more than about 0.05 mAh/$cm^2$ that is twice the cathode capacity of $LiCoO_2$ obtained with a similar volume of $LiCoO_2$ to $Li_2O_2$. The present embodiments furthermore provide a gravimetric energy density per cathode mass that is two thousand times higher than that of $LiCoO_2$ and four times higher per cathode mass when the weight of discharge products are included.

Figure 1:
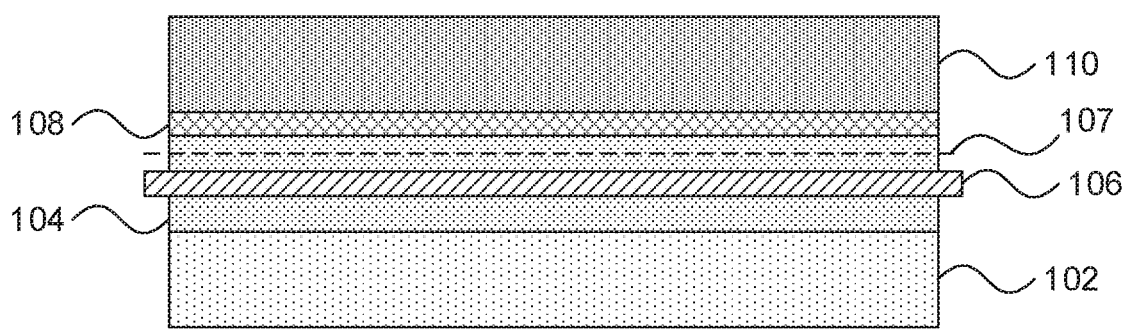
FIG. 1 is a cross-sectional diagram of a lithium-oxygen battery having a thin graphene cathode in accordance with an embodiment of the present invention.

Referring now to FIG. 1, a cross-sectional view of a lithium-oxygen battery 100 is shown. An anode 102 is separated from a cathode 108 by an electrolyte 104 and separator 106. The electrolyte 104 provides a conductive channel for the movement of charge carriers from the anode 102 to the cathode 108 during discharge reaction. The separator 106 is a non-conductive, porous structure that prevents the anode 102 and cathode 108 from coming into electrical contact with one another. In some embodiments, the electrolyte 104 is a fluid. In other embodiments, the electrolyte 104 is a solid material that also plays the role of separator 106. The cathode 108 is formed on a substrate layer 110 that may be flexible or rigid, conductive or non-conductive, flat or rough, and that is used to transfer the cathode 108.

In one specific embodiment, the anode 102 is formed from a layer of lithium metal, but it should be understood that other materials such as, e.g., sodium or other alkaline metals, may be used instead. In one specific embodiment, the cathode 108 is formed from graphene, a very thin species of carbon that can be formed to a thickness of a single atom. In one specific embodiment, the separator 106 may be a porous polymeric film such as, e.g., polyethylene or polypropylene or quartz ($SiO_2$) microfiber filters, and may be formed at a thickness between about 25 μm and 450 μm. In embodiments with mechanically strong, solid-state electrolytes (which can function as a separator) 104 may be as thin as hundreds of nanometers. In one specific embodiment, the substrate 110 may be formed from, e.g., a silicon or silicon dioxide wafer, a stainless steel pad, glass, or a polyimide film.

In one specific embodiment, the electrolyte 104 is formed from an appropriate liquid electrolyte material such as, e.g., a solution that has $LiNO_3$ or (Lithium Bis(trifluoromethanesulfonyl)imide) (LiTFSI) as salts, mixed with 1,2-dimethoxyethane (DME) or tetraethylene glycol dimethyl ether (TEGDME) as solvents. The electrolyte enhances battery capacity in single- and double-layer graphene cathodes and have a high solubility of intermediate species (e.g., $Li^+$ and $O_2^-$) during the formation of $Li_2O_2$. Because the intermediate species can dissolve into the electrolyte during discharge, those species can migrate farther to form larger particles of $Li_2O_2$, rather than precipitating into a film and passivating the cathode surface. Such electrolytes may further include small amounts of water.

A current collector 107 is positioned in the electrolyte 104 and may, in some embodiments, be formed from stainless steel or titanium. It is specifically contemplated that the current collector 107 may be formed from, e.g., a conductive wire mesh formed from any appropriate metal or other conductor that will not react with the electrolyte 104 or otherwise corrode. The current collector 107 may include a mesh that has openings smaller than about 38 µm. This sizing represents just one example—a finer mesh will provide better electron distribution. The current collector 107 leaves the battery 100 to connect to an external circuit.

It should be understood that the present embodiments illustrate only one possible example of the use of a thin carbon cathode in a battery. It is specifically contemplated that, in this embodiment, the cathode 108 may be formed on a layer of copper by, e.g., chemical vapor deposition (CVD) or any other appropriate mechanism. For example, a layer of graphene may be formed on the copper layer by carbon CVD, where the atoms of carbon self-organize into a flat sheet that is one or more atoms thick.

Some embodiments may employ the copper layer directly as the substrate 110. However, experimental evidence has shown that a graphene/copper electrode shows $Li_2O_2$ formation until 2.1V, followed by electrochemical reactions from the copper at potentials below 2.1V. Thus, the present embodiments transfer the graphene to an alternative substrate material. The cathode 108 may therefore be mounted to an intermediate handling layer formed from, e.g., poly(methyl methacrylate) (PMMA), ethylene-vinyl acetate (EVA), or any other appropriate material that has etch selectivity with the copper layer. The copper layer is then etched away using, e.g., $FeCl_3$, allowing the cathode 108 to be moved to the substrate layer 110. The handling layer is then etched away using, e.g., acetone for PMMA or xylene for EVA, and the substrate 110 and cathode 108 can be affixed to the battery 100. This process for creating and transporting the cathode 108 has an advantage in that it does not need a high-temperature anneal, the way lithium-ion cathodes do, and in that the cathode 108 can be transferred to non-conducting or conducting surface. However, this illustrates just one possible process for forming a thin cathode layer—any other appropriate process can be used instead. In some embodiments, the cathode may be about 1 nm and about 2 nm thick.

During operation of a lithium-oxygen battery, lithium ions diffuse across the electrolyte from the anode 102 to the cathode 108, where it reacts with oxygen at the cathode 108 and forms $Li_2O_2$. This movement of positive ions is accompanied by a flow of electrons in the current collector 107 toward the device 100, representing a discharging action. The $Li_2O_2$ accumulates on the surface of the cathode 108 during this discharging action.

Figure 2:
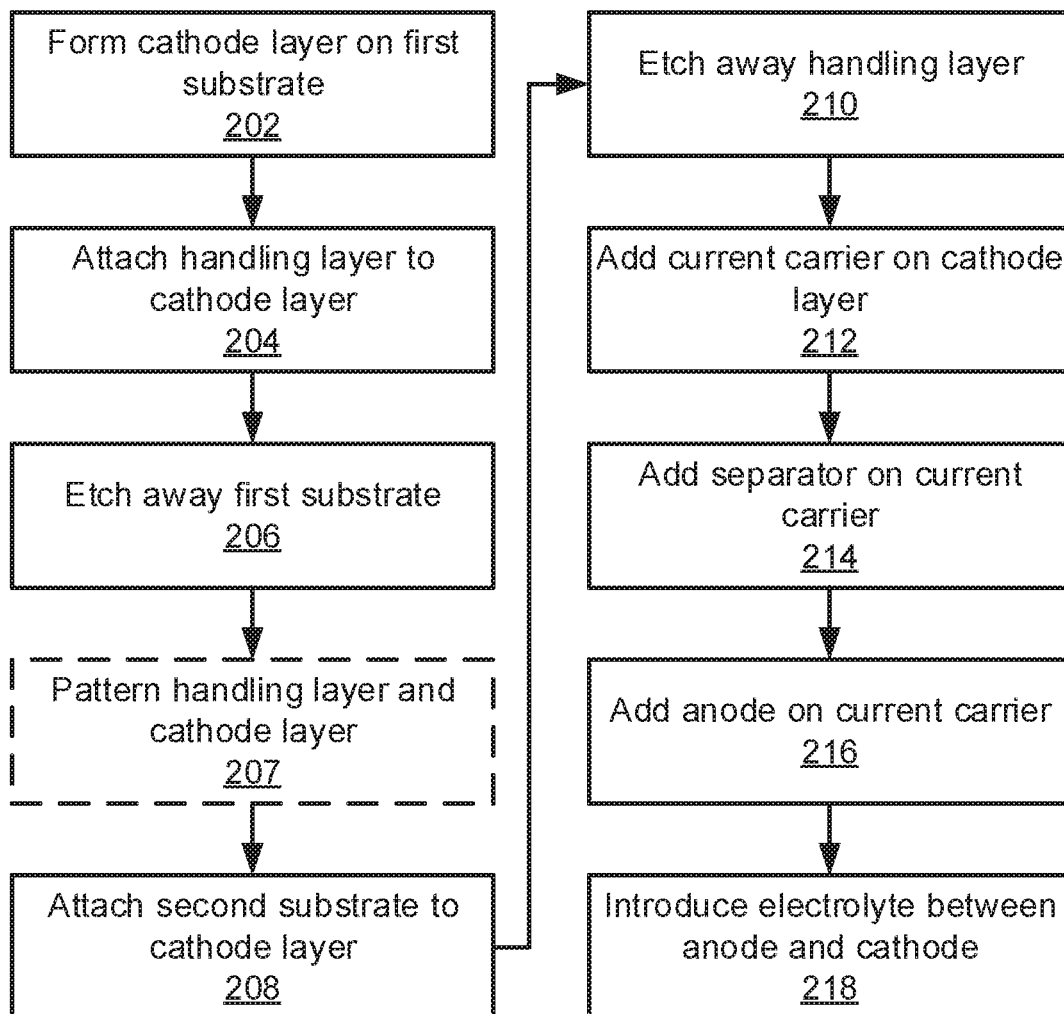
FIG. 2 is a block/flow diagram of a method of forming a lithium-oxygen battery having a thin graphene cathode in accordance with an embodiment of the present invention.

Referring now to FIG. 2, a method of fabricating a battery is shown. Block 202 forms the cathode 108 on a first substrate. As noted above, it is specifically contemplated that the cathode 108 may be formed from graphene and may be very thin (e.g., between about 1 nm and 2 nm) and that the first substrate may be, e.g., copper or nickel. The cathode 108 may be formed by CVD or any other appropriate deposition process that allows atoms of the cathode material (e.g., carbon) so self-organize on the surface of the first substrate.

CVD is a deposition process in which a deposited species is formed as a result of chemical reaction between gaseous reactants at greater than room temperature (e.g., from about 25° C. about 900° C.). The solid product of the reaction is deposited on the surface on which a film, coating, or layer of the solid product is to be formed. Variations of CVD processes include, but are not limited to, Atmospheric Pressure CVD (APCVD), Low Pressure CVD (LPCVD), Plasma Enhanced CVD (PECVD), and Metal-Organic CVD (MOCVD) and combinations thereof may also be employed.

Block 204 attaches a handling layer to the cathode layer 108. It is specifically contemplated that the handling layer may be formed from, e.g., PMMA, but it should be understood that any material having etch selectivity with the first and second substrates and the cathode 108 may be used instead. The handling layer may be applied by any appropriate mechanism including, e.g., spin coating. As used herein, the term "selective" in reference to a material removal process denotes that the rate of material removal for a first material is greater than the rate of removal for at least another material of the structure to which the material removal process is being applied.

Block 206 then etches away the first substrate using an appropriate wet or dry etch such as, e.g., $FeCl_3$. The cathode 108 remains attached to the handling layer and can be moved into position over a second substrate (which forms substrate 110 of the finished battery 100). The cathode 108 covered by the second substrate can optionally be patterned in block 207 using the handling layer as a photoresist. The cathode surface that is not covered by the handling layer can be selectively removed. In the example where the cathode 108 is formed from graphene and the handling layer is formed from PMMA, the graphene cathode can be etched using an oxygen plasma. This is a simpler process than patterning inorganic cathodes formed from, e.g., $LiCoO_2$, $LiFePO_4$, or $LiNi_xMn_yCo_zO_2$ because they require harsh chemical etching methods. Building arrays of batteries and the accompanying circuit design is similarly simplified by simple micropatterning of graphene based cathodes, in particular for micron scale devices.

The cathode 108 is attached to the second substrate in block 208. No adhesive may be needed to attach the cathode 108 to the second substrate—instead an attractive force is present due to, e.g., Van der Waals interactions. The handling layer is then etched away using any appropriate wet or dry etchant such as, e.g., acetone, leaving the cathode 108 on the substrate 110.

Block 212 adds a current carrier 107 in the form of a conductive mesh on top of the cathode layer 108. Block 214 adds a separator 106 on the current carrier 107, covering the current carrier 107 and the cathode layer 108. The separator may be formed from, e.g., a thin sheet of porous membrane. Block 216 adds anode 102 on the separator 106. The anode 102 is formed from an appropriate metal such as, e.g., lithium, $LiC_6$, $Li_7Ti_5O_{12}$, or $Li_{4.4}Si$. Block 218 then introduces a liquid electrolyte between the anode 102 and the cathode 108. It is specifically contemplated that the electrolyte may be formed from $LiNO_3$ or LiTFSI as salts mixed in an ether-based solvent (e.g., DME, TEGDME), but any appropriate electrolyte composition may be used instead.

It is to be understood that aspects of the present invention will be described in terms of a given illustrative architecture; however, other architectures, structures, substrate materials and process features and steps can be varied within the scope of aspects of the present invention.

Figure 3:
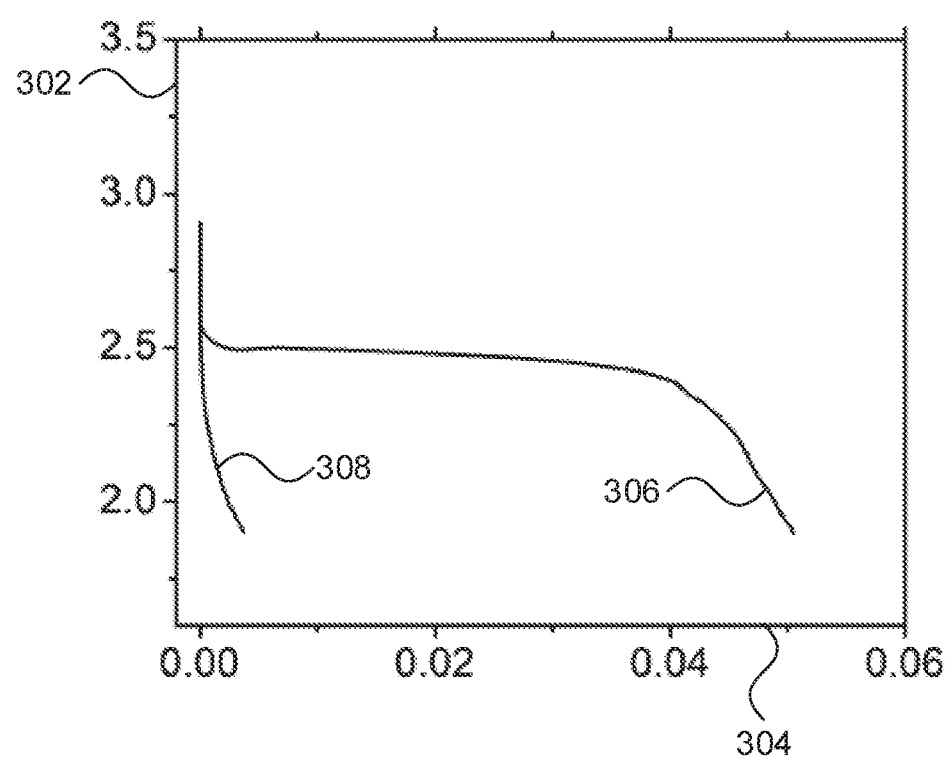
FIG. 3 is a graph illustrating the effect of using a thin graphene cathode in a lithium-oxygen battery as compared to the use of a bare substrate in accordance with an embodiment of the present invention.

Referring now to FIG. 3, a graph of the relationship between cell voltage on the vertical axis 302, measured in Volts, and charge capacity on the horizontal axis 304, measured in $mAh/cm^2$ at the current density of 4 $\mu A/cm^2$, is shown for two different cathode materials in a DME-based electrolyte mixed with $LiNO_3$ to facilitate solution-mediated lithium-oxygen battery discharge reactions. A bare silicon or silicon dioxide layer is shown by curve 308 and a graphene layer mounted on a silicon or silicon dioxide layer is shown by curve 306. Those cathodes were tested against lithium metal as anode. A flat voltage profile is shown around 2.5V for curve 306, but no significant discharge capacity is provided by the bare wafer. Similar results are provided by electrolyte solutions based on TEGDME.

The discharge products of the discharge reaction are confirmed to be $Li_2O_2$ by measuring the Raman spectrum (e.g., using a 532 nm laser) of pristine and discharged graphene cathodes. A peak at about 790 $cm^{-1}$ appears after discharge, corresponding to O—O bond stretching in $Li_2O_2$. The growth of $Li_2O_2$ is enabled by having a single/double layer of graphene. The graphene surface can function as a seed for $Li_2O_2$ growth even in the presence of a non-conducting substrate 110. With a TEGDME electrolyte and a 0.5M $LiNO_3$ solution the present embodiments can provide about 60 $\mu Ah/cm^2$ of capacity at 24 $\mu A/cm^2$ of current density.

It will also be understood that when an element such as a layer, region or substrate is referred to as being "on" or "over" another element, it can be directly on the other element or intervening elements can also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements can be present. In contrast, when an element is referred to as being "directly connected" or "directly coupled" to another element, there are no intervening elements present.

The present embodiments can include a design for an integrated circuit chip, which can be created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer can transmit the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

Methods as described herein can be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multichip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

It should also be understood that material compounds will be described in terms of listed elements, e.g., SiGe. These compounds include different proportions of the elements within the compound, e.g., SiGe includes $Si_xGe_{1-x}$ where x is less than or equal to 1, etc. In addition, other elements can be included in the compound and still function in accordance with the present principles. The compounds with additional elements will be referred to herein as alloys.

Reference in the specification to "one embodiment" or "an embodiment", as well as other variations thereof, means that a particular feature, structure, characteristic, and so forth described in connection with the embodiment is included in at least one embodiment. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This can be extended, as readily apparent by one of ordinary skill in this and related arts, for as many items listed.

The terminology used herein s for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Spatially relative terms, such as "beneath," "below," "lower," "above," "upper," and the like, can be used herein for ease of description to describe one element's or feature's relationship to another element(s) or feature(s) as illustrated in the FIGS. It will be understood that the spatially relative terms are intended to encompass different orientations of the device in use or operation in addition to the orientation depicted in the FIGS. For example, if the device in the FIGS. is turned over, elements described as "below" or "beneath" other elements or features would then be oriented "above" the other elements or features. Thus, the term "below" can encompass both an orientation of above and below. The device can be otherwise oriented (rotated 90 degrees or at other orientations), and the spatially relative descriptors used herein can be interpreted accordingly. In addition, it will also be understood that when a layer is referred to as being "between" two layers, it can be the only layer between the two layers, or one or intervening layers can also be present.

It will be understood that, although the terms first, second, etc. can be used herein to describe various elements, these elements should not be limited by these terms. These terms are only used to distinguish one element from another element. Thus, a first element discussed below could be termed a second element without departing from the scope of the present concept.

Having described preferred embodiments of a system and method (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A battery, comprising:
   an anode;
   an electrolyte having a high solubility for lithium ions and oxygen;
   a cathode formed on a substrate, such that lithium ions migrate from the anode through the electrolyte to form Li2O2 at a surface of the cathode, and
   a current collector positioned in the electrolyte, the electrolyte separating the anode from the cathode.

2. The battery of claim 1, wherein the cathode is a material selected from the group consisting of single-layer graphene and double-layer graphene.

3. The battery of claim 1, wherein the electrolyte comprises 1,2-dimethoxyethane.

4. The battery of claim 1, wherein the electrolyte comprises tetraethylene glycol dimethyl ether.

5. The battery claim 1, wherein the electrolyte comprises a solute selected from the group consisting of LiNO3 and (Lithium Bis(trifluoromethanesulfonyl)imide).

6. The battery of claim 1, wherein the current collector is positioned between the cathode and a separator.

7. The battery of claim 6, wherein the current collector is a metal mesh formed from a material selected from the group consisting of stainless steel and titanium.

8. The battery of claim 7, wherein the metal mesh has openings that are smaller than about 38 μm.

9. The battery of claim 1, wherein the cathode is a self-organized flat sheet.

10. The battery of claim 1, wherein the substrate is flexible.

11. The battery of claim 1, wherein the electrolyte is a fluid and the current collector connects to an external circuit.

12. A battery, comprising:
    an anode;
    an electrolyte having a high solubility for lithium ions and oxygen;
    a current collector in the electrolyte formed from a metal mesh; and
    a cathode formed on a substrate from a single- or double-layer graphene material, such that lithium ions migrate from the anode through the electrolyte to form Li2O2 at a surface of the cathode.

13. The battery of claim 12, wherein the electrolyte is selected from the group consisting of 1,2-dimethoxyethane and tetraethylene glycol dimethyl ether.

14. The battery of claim 12, wherein the electrolyte comprises a solute selected from the group consisting of LiNO3 and (Lithium Bis(trifluoromethanesulfonyl)imide).

15. The battery of claim 12, wherein the substrate is flexible.

16. The battery of claim 12, wherein the electrolyte separates the anode from the cathode.

17. The battery of claim 12, wherein the graphene cathode is a self-organized flat sheet.

18. The battery of claim 12, wherein the current collector is a metal mesh formed from a material selected from the group consisting of stainless steel and titanium.

19. The battery of claim 12, wherein the metal mesh has openings that are smaller than about 38 μm.

20. The battery of claim 12, wherein the electrolyte is a fluid and the current collector connects to an external circuit.

* * * * *